M

(12) United States Patent
Danielsen et al.

(10) Patent No.: US 8,709,773 B2
(45) Date of Patent: Apr. 29, 2014

(54) **DFPASE ENZYMES FROM *APLYSIA CALIFORNICA***

(75) Inventors: Steffen Danielsen, Dyssegaard (DK); Lars Kobberoee Skov, Ballerup (DK); Ricardo Leite, Faro (PT); Vincent Laizé, Faro (PT); M Leonor Cancela Da Fonseca, Faro (PT)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 13/319,282

(22) PCT Filed: May 6, 2010

(86) PCT No.: PCT/EP2010/056205
§ 371 (c)(1),
(2), (4) Date: Apr. 19, 2012

(87) PCT Pub. No.: WO2010/128116
PCT Pub. Date: Nov. 11, 2010

(65) Prior Publication Data
US 2012/0195874 A1   Aug. 2, 2012

Related U.S. Application Data

(60) Provisional application No. 61/176,609, filed on May 8, 2009.

(30) Foreign Application Priority Data

May 6, 2009 (EP) .................................. 09159516

(51) Int. Cl.
| | | |
|---|---|---|
| C12N 9/16 | (2006.01) | |
| C12N 9/14 | (2006.01) | |
| A61K 38/46 | (2006.01) | |
| C12P 21/06 | (2006.01) | |
| C12P 19/34 | (2006.01) | |
| C12N 15/00 | (2006.01) | |
| C12N 1/20 | (2006.01) | |
| C12N 1/00 | (2006.01) | |
| C07H 21/04 | (2006.01) | |
| C07K 1/00 | (2006.01) | |

(52) U.S. Cl.
USPC .......... 435/196; 435/195; 435/69.1; 435/91.1; 435/320.1; 435/252.3; 435/254.11; 424/94.6; 536/23.2; 536/23.1; 530/350

(58) Field of Classification Search
USPC ......... 435/196, 195, 69.1, 91.1, 320.1, 252.3, 435/254.11; 424/94.6; 536/23.2, 23.1; 530/350
See application file for complete search history.

(56) References Cited

U.S. PATENT DOCUMENTS 6,524,834 B1 * 2/2003 Ruterjans et al. .............. 435/196

FOREIGN PATENT DOCUMENTS

| WO | 9943791 A2 | 11/1999 |
| WO | 2008036061 A2 | 3/2008 |

OTHER PUBLICATIONS

Broun et al., Catalytic plasticity of fatty acid modification enzymes underlying chemical diversity of plant lipids. Science, 1998, vol. 282: 1315-1317.*
Chica et al., Semi-rational approaches to engineering enzyme activity: combining the benefits of directed evolution and rational design. Curr. Opi. Biotechnol., 2005, vol. 16: 378-384.*
Devos et al., Practical limits of function prediction. Proteins: Structure, Function, and Genetics. 2000, vol. 41: 98-107.*
Seffernick et al., Melamine deaminase and Atrazine chlorohydrolase: 98 percent identical but functionally different. J. Bacteriol., 2001, vol. 183 (8): 2405-2410.*
Sen et al., Developments in directed evolution for improving enzyme functions. Appl. Biochem. Biotechnol., 2007, vol. 143: 212-223.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Database EMBL—Access No. FF061286 (2008).
Database EMBL—Access No. FF075203 (2008).
Database UniProt—Access No. Q7SIG4 (2009).
Hartleib et al, Biochimica et Biophysica Acta 1546 (2), 312-324 (2001).
Scharff et al, Structure 9 (6), 493-502 (2001).

* cited by examiner

Primary Examiner — Ganapathirama Raghu
(74) Attorney, Agent, or Firm — Michael W. Krenicky

(57) ABSTRACT

The present invention relates to isolated polypeptides having organophosphorous hydrolase activity and isolated polynucleotides encoding the polypeptides. The invention also relates to nucleic acid constructs, vectors, and host cells comprising the polynucleotides as well as methods of producing and using the polypeptides.

17 Claims, 1 Drawing Sheet

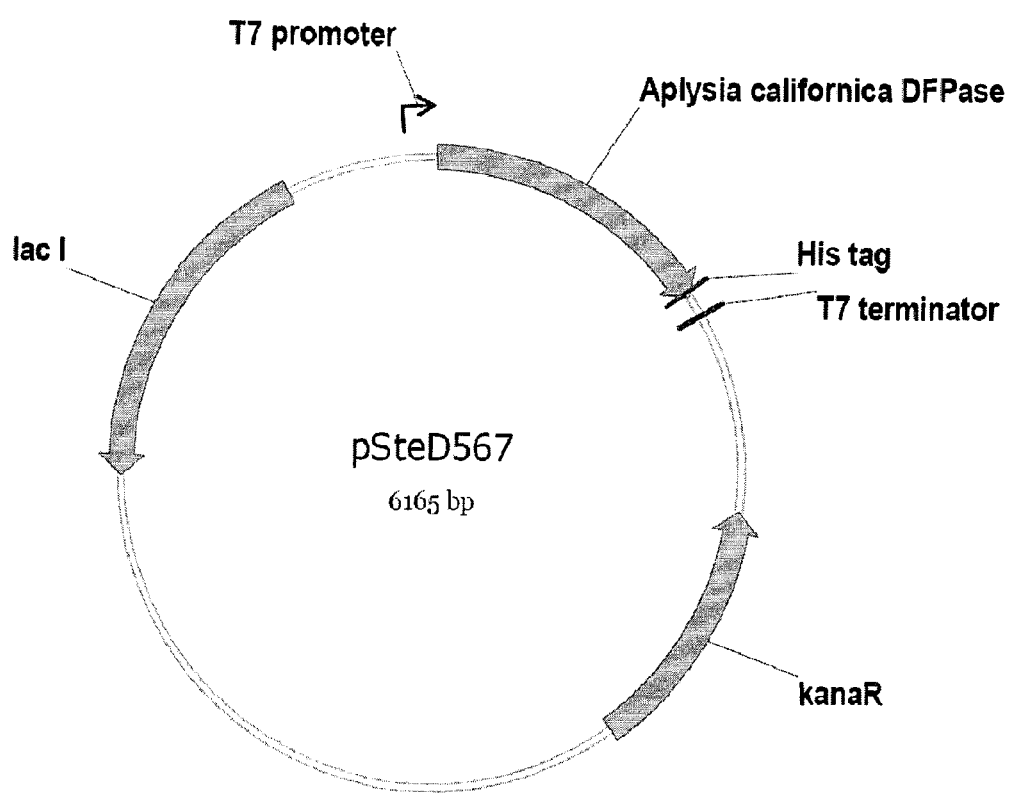

DFPASE ENZYMES FROM *APLYSIA CALIFORNICA*

CROSS-REFERENCE TO RELATED APPLICATIONS

This application is a 35 U.S.C. 371 national application of PCT/EP2010/056205 filed May 6, 2010, which claims priority or the benefit under 35 U.S.C. 119 of European application no. 09159516.5 filed May 6, 2009 and U.S. provisional application No. 61/176,609 filed May 8, 2009, the contents of which are fully incorporated herein by reference.

REFERENCE TO A SEQUENCE LISTING

This application contains a Sequence Listing in computer readable form. The computer readable form is incorporated herein by reference.

REFERENCE TO A DEPOSIT OF BIOLOGICAL MATERIAL

This application contains a reference to a deposit of biological material, which deposit is incorporated herein by reference. For complete information see last paragraph of the description.

BACKGROUND OF THE INVENTION

1. Field of the Invention

The present invention relates to isolated polypeptides having organophosphorous hydrolase activity and isolated polynucleotides encoding the polypeptides. The invention also relates to nucleic acid constructs, vectors, and host cells comprising the polynucleotides as well as methods of producing and using the polypeptides.

2. Description of the Related Art

Organophosphorous compounds are known in the art. In particular some warfare agents are known to be organophosphorous compounds such as Sarin, Cyclosarin, and Soman. Other organophosphorous compounds are known as pesticides.

It is desirable to be able to decontaminate areas contaminated with such organophosphorous compounds. A polypeptide having organophosphorous hydrolase activity, such as diisopropylfluorophosphatase activity has been suggested for this purpose since such polypeptides are capable of hydrolyzing harmful organophosphorous compounds and thereby converting them to less harmful products.

In WO99/43791 a diisopropylfluorophosphatase from *Loligo vulgaris* is disclosed and its potential use for decontamination among other applications is also described.

It is an object of the present invention to provide polypeptides having organophosphorous hydrolase e.g. diisopropylfluorophosphatase activity and polynucleotides encoding the polypeptides, in particular having high stability and for high specific activity.

SUMMARY OF THE INVENTION

The present invention relates to isolated polypeptides having organophosphorous hydrolase activity, selected from the group consisting of:
(a) a polypeptide comprising an amino acid sequence having at least 75%, more preferably at least 80%, even more preferably at least 85%, most preferably at least 90%, and even most preferably at least 95% identity to the mature polypeptide of SEQ ID NO: 2;
(b) a polypeptide encoded by a polynucleotide that hybridizes under at least medium-high stringency conditions with (i) the mature polypeptide coding sequence of SEQ ID NO: 1, (ii) a DNA sequence comprising the mature polypeptide coding sequence of SEQ ID NO: 1, or (iii) a full-length complementary strand of (i) or (ii);
(c) a polypeptide encoded by a polynucleotide comprising a nucleotide sequence having at least 65%, more preferably at least 70%, more preferably at least 75%, more preferably at least 80%, more preferably at least 85%, more preferably at least 90%, more preferably at least 95%, more preferably at least 96%, even more preferably at least 97%, most preferably at least 98% and even most preferably 99% identity to the mature polypeptide coding sequence of SEQ ID NO: 1;
(d) a variant comprising a substitution, deletion, and/or insertion of one or more (several) amino acids of the mature polypeptide of SEQ ID NO: 2.

The present invention also relates to isolated polynucleotides encoding polypeptides having organophosphorous hydrolase activity, selected from the group consisting of:
(a) a polynucleotide encoding a polypeptide comprising an amino acid sequence having at least 75% identity to the mature polypeptide of SEQ ID NO: 2;
(b) a polynucleotide that hybridizes under at least medium stringency conditions with (i) the mature polypeptide coding sequence of SEQ ID NO: 1, (ii) a DNA sequence comprising the mature polypeptide coding sequence of SEQ ID NO: 1, or (iii) a full-length complementary strand of (i) or (ii);
(c) a polynucleotide comprising a nucleotide sequence having at least 65% identity to the mature polypeptide coding sequence of SEQ ID NO: 1; and
(d) a polynucleotide encoding a variant comprising a substitution, deletion, and/or insertion of one or more (several) amino acids of the mature polypeptide of SEQ ID NO: 2.

The present invention also relates to nucleic acid constructs, recombinant expression vectors, recombinant host cells comprising the polynucleotides, and methods of producing a polypeptide having organophosphorous hydrolase activity.

The present invention also relates to methods of decontamination, e.g. by degrading organophosphorous compounds.

In particular the present invention relates to methods of decontaminating an area or a device contaminated with one or more hazardous or undesired organophosphorous compounds by applying the organophosphorous hydrolase of the invention to said area or device.

The present invention also relates to plants comprising an isolated polynucleotide encoding such a polypeptide having organophosphorous hydrolase activity.

The present invention also relates to methods of producing such a polypeptide having organophosphorous hydrolase activity, comprising: (a) cultivating a transgenic plant or a plant cell comprising a polynucleotide encoding such a polypeptide having organophosphorous hydrolase activity under conditions conducive for production of the polypeptide; and (b) recovering the polypeptide.

BRIEF DESCRIPTION OF THE FIGURES

FIG. 1 shows restriction map of NN059104.

DEFINITIONS

The term "Organophosphorous hydrolase activity" is defined herein as hydrolytic activity to organophosphorous compounds, in particular phosphorous anhydride bonds in organophosphorous compounds including nerve gases. Thus the term includes an enzyme with hydrolase activity and/or esterase activity, e.g. organophosphorous hydrolase activity (EC 3.1.8.1) (such as an organophosphoesterase activity) or organophosphoric acid anhydrolase (OPAA) activity, or carboxylesterase activity, diisopropylfluorophosphatase (DFPase) activity (EC 3.1.8.2), dehalogenase activity, prolidase activity and/or imidodipeptidase activity.

The term "DFPase (EC3.1.8.2)" is defined herein as diisopropylfluorophosphatase, dialkylfluorophosphatase, diisopropyl phosphorofluoridate hydrolase, diisopropylfluorophosphonate dehalogenase, diisopropylphosphofluoridase, isopropylphosphorofluoridase, organophosphate acid anhydrase, organophosphorous acid anhydrolase, somanase, tabunase. DFPases acts on phosphorus anhydride bonds (such as phosphorus-halide and phosphorus-cyanide) in organophosphorous compounds (including nerve gases).

The activity of the polypeptides according to the invention is measured as described in Example 3 "Measurement of enzyme activity". The polypeptides of the present invention have at least 20%, preferably at least 40%, more preferably at least 50%, more preferably at least 60%, more preferably at least 70%, more preferably at least 80%, even more preferably at least 90%, most preferably at least 95%, most preferably at least 100%, or even more preferably above 100% such as 110%, or 120% or 130%, or 140% or even more preferably at least or above 150% of the organophosphorous hydrolase activity of the mature polypeptide of SEQ ID NO: 2.

Decontamination activity: The term "decontamination activity" is to be understood herein as removing harmful agents such as organophosphorous compounds, e.g. nerve gases, toxins, pesticides, thus the term includes e.g. detoxification activity.

Isolated polypeptide: The term "isolated polypeptide" as used herein refers to a polypeptide that is isolated from a source. In a preferred aspect, the polypeptide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by SDS-PAGE.

Substantially pure polypeptide: The term "substantially pure polypeptide" denotes herein a polypeptide preparation that contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polypeptide material with which it is natively or recombinantly associated. It is, therefore, preferred that the substantially pure polypeptide is at least 92% pure, preferably at least 94% pure, more preferably at least 95% pure, more preferably at least 96% pure, more preferably at least 96% pure, more preferably at least 97% pure, more preferably at least 98% pure, even more preferably at least 99% pure, most preferably at least 99.5% pure, and even most preferably 100% pure by weight of the total polypeptide material present in the preparation. The polypeptides of the present invention are preferably in a substantially pure form, i.e., that the polypeptide preparation is essentially free of other polypeptide material with which it is natively or recombinantly associated. This can be accomplished, for example, by preparing the polypeptide by well-known recombinant methods or by classical purification methods.

Mature polypeptide: The term "mature polypeptide" is defined herein as a polypeptide having organophosphorous hydrolase activity that is in its final form following translation and any post-translational modifications, such as N-terminal processing, C-terminal truncation, glycosylation, phosphorylation etc.

Mature polypeptide coding sequence: The term "mature polypeptide coding sequence" is defined herein as a nucleotide sequence that encodes a mature polypeptide having organophosphorous hydrolase activity.

Identity: The relatedness between two amino acid sequences or between two nucleotide sequences is described by the parameter "identity".

For purposes of the present invention, the degree of identity between two amino acid sequences is determined using the Needleman-Wunsch algorithm (Needleman and Wunsch, 1970, *J. Mol. Biol.* 48: 443-453) as implemented in the Needle program of the EMBOSS package (EMBOSS: The European Molecular Biology Open Software Suite, Rice et al., 2000, *Trends in Genetics* 16: 276-277), preferably version 3.0.0 or later. The optional parameters used are gap open penalty of 10, gap extension penalty of 0.5, and the EBLOSUM62 (EMBOSS version of BLOSUM62) substitution matrix. The output of Needle labeled "longest identity" (obtained using the—nobrief option) is used as the percent identity and is calculated as follows:

(Identical Residues×100)/(Length of Alignment−Total Number of Gaps in Alignment)

For purposes of the present invention, the degree of identity between two deoxyribonucleotide sequences is determined using the Needleman-Wunsch algorithm (Needleman and Wunsch, 1970, supra) as implemented in the Needle program of the EMBOSS package (EMBOSS: The European Molecular Biology Open Software Suite, Rice et al., 2000, supra), preferably version 3.0.0 or later. The optional parameters used are gap open penalty of 10, gap extension penalty of 0.5, and the EDNAFULL (EMBOSS version of NCBI NUC4.4) substitution matrix. The output of Needle labeled "longest identity" (obtained using the—nobrief option) is used as the percent identity and is calculated as follows:

(Identical Deoxyribonucleotides×100)/(Length of Alignment−Total Number of Gaps in Alignment)

Homologous sequence: The term "homologous sequence" is defined herein as a predicted protein that gives an E value (or expectancy score) of less than 0.001 in a tfasty search (Pearson, W. R., 1999, in *Bioinformatics Methods and Protocols*, S. Misener and S. A. Krawetz, ed., pp. 185-219) with the *Aplysia californica* organophosphorous hydrolase according to the invention.

Polypeptide fragment: The term "polypeptide fragment" is defined herein as a polypeptide having one or more (several) amino acids deleted from the amino and/or carboxyl terminus of the mature polypeptide of SEQ ID NO: 2; or a homologous sequence thereof; wherein the fragment has organophosphorous hydrolase activity.

Subsequence: The term "subsequence" is defined herein as a nucleotide sequence having one or more (several) nucleotides deleted from the 5' and/or 3' end of the mature polypeptide coding sequence of SEQ ID NO: 1; or a homologous sequence thereof; wherein the subsequence encodes a polypeptide fragment having organophosphorous hydrolase activity.

Allelic variant: The term "allelic variant" denotes herein any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

Isolated polynucleotide: The term "isolated polynucleotide" as used herein refers to a polynucleotide that is isolated from a source. In a preferred aspect, the polynucleotide is at least 1% pure, preferably at least 5% pure, more preferably at least 10% pure, more preferably at least 20% pure, more preferably at least 40% pure, more preferably at least 60% pure, even more preferably at least 80% pure, and most preferably at least 90% pure, as determined by agarose electrophoresis.

Substantially pure polynucleotide: The term "substantially pure polynucleotide" as used herein refers to a polynucleotide preparation free of other extraneous or unwanted nucleotides and in a form suitable for use within genetically engineered protein production systems. Thus, a substantially pure polynucleotide contains at most 10%, preferably at most 8%, more preferably at most 6%, more preferably at most 5%, more preferably at most 4%, more preferably at most 3%, even more preferably at most 2%, most preferably at most 1%, and even most preferably at most 0.5% by weight of other polynucleotide material with which it is natively or recombinantly associated. A substantially pure polynucleotide may, however, include naturally occurring 5' and 3' untranslated regions, such as promoters and terminators. It is preferred that the substantially pure polynucleotide is at least 90% pure, preferably at least 92% pure, more preferably at least 94% pure, more preferably at least 95% pure, more preferably at least 96% pure, more preferably at least 97% pure, even more preferably at least 98% pure, most preferably at least 99%, and even most preferably at least 99.5% pure by weight. The polynucleotides of the present invention are preferably in a substantially pure form, i.e., that the polynucleotide preparation is essentially free of other polynucleotide material with which it is natively or recombinantly associated. The polynucleotides may be of genomic, cDNA, RNA, semisynthetic, synthetic origin, or any combinations thereof.

Coding sequence: When used herein the term "coding sequence" means a nucleotide sequence, which directly specifies the amino acid sequence of its protein product. The boundaries of the coding sequence are generally determined by an open reading frame, which usually begins with the ATG start codon or alternative start codons such as GTG and TTG and ends with a stop codon such as TAA, TAG, and TGA. The coding sequence may be a DNA, cDNA, synthetic or recombinant nucleotide sequence.

DNA: The term "DNA" as used herein refers to all DNA, thus the DNA may be synthetic, genomic DNA or cDNA, which is defined herein as a DNA molecule that can be prepared by reverse transcription from a mature, spliced, mRNA molecule obtained from a eukaryotic cell. cDNA lacks intron sequences that are usually present in the corresponding genomic DNA. The initial, primary RNA transcript is a precursor to mRNA that is processed through a series of steps before appearing as mature spliced mRNA. These steps include the removal of intron sequences by a process called splicing. cDNA derived from mRNA lacks, therefore, any intron sequences.

Nucleic acid construct: The term "nucleic acid construct" as used herein refers to a nucleic acid molecule, either single- or double-stranded, which is isolated from a naturally occurring gene or which is modified to contain segments of nucleic acids in a manner that would not otherwise exist in nature or which is synthetic. The term nucleic acid construct is synonymous with the term "expression cassette" when the nucleic acid construct contains the control sequences required for expression of a coding sequence of the present invention.

Control sequences: The term "control sequences" is defined herein to include all components necessary for the expression of a polynucleotide encoding a polypeptide of the present invention. Each control sequence may be native or foreign to the nucleotide sequence encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleotide sequence encoding a polypeptide.

Operably linked: The term "operably linked" denotes herein a configuration in which a control sequence is placed at an appropriate position relative to the coding sequence of the polynucleotide sequence such that the control sequence directs the expression of the coding sequence of a polypeptide.

Expression: The term "expression" includes any step involved in the production of the polypeptide including, but not limited to, transcription, post-transcriptional modification, translation, post-translational modification, and secretion.

Expression vector: The term "expression vector" is defined herein as a linear or circular DNA molecule that comprises a polynucleotide encoding a polypeptide of the present invention and is operably linked to additional nucleotides that provide for its expression.

Host cell: The term "host cell", as used herein, includes any cell type that is susceptible to transformation, transfection, transduction, and the like with a nucleic acid construct or expression vector comprising a polynucleotide of the present invention.

Modification: The term "modification" means herein any chemical modification of the polypeptide consisting of the mature polypeptide of SEQ ID NO: 2; or a homologous sequence thereof; as well as genetic manipulation of the DNA encoding such a polypeptide. The modification can be a substitution, a deletion and/or an insertion of one or more (several) amino acids as well as replacements of one or more (several) amino acid side chains.

Artificial variant: When used herein, the term "artificial variant" means a polypeptide having organophosphorous hydrolase activity produced by an organism expressing a modified polynucleotide sequence of the mature polypeptide coding sequence of SEQ ID NO: 1; or a homologous sequence thereof. The modified nucleotide sequence is obtained through human intervention by modification of the polynucleotide sequence disclosed in SEQ ID NO: 1; or a homologous sequence thereof.

DETAILED DESCRIPTION OF THE INVENTION

Polypeptides Having Organophosphorous Hydrolase Activity

The present invention provides novel polypeptides having hydrolase activity, an esterase activity e.g. organophosphorous hydrolase activity or organophosphorous acid anhydrolase (OPAA) activity or preferably diisopropylfluorophosphatase (DFPase) activity. The present invention further relates to use of these polypeptides for decontamination of toxins, poisons, such as nerve gases e.g. of the Vx or Gx type and pesticides.

The polypeptide according to the invention has at least one enzyme activity, such as hydrolysis of, or decontamination of, V agents, or G agents and/or pesticides.

The V agent may comprise VX (O-Ethyl-S-[2(diisopropylamino)ethyl]methylphosphonothioate, or methylphosphonothioic acid), VE (O-Ethyl-S-[2-(diethylamino)ethyl]ethylphosphonothioate), VG (O,O-Diethyl-S-[2-(diethylamino)ethyl]phosphorothioate), VM (0-Ethyl-S-[2-(diethylamino)ethyl]methylphosphonothioate), VR (Phosphonothioic acid) Soviet V-gas (Russian VX), Tetriso (0,0-diisopropyl S-(2-diisopropylaminoethyl) phosphorothiolate).

The G agent may comprise tabun (GA), sarin (methylphosphonofluoridic acid) (GB), soman (GD), cyclosarin (GF) or a combination thereof.

The pesticides may comprise fungicides, insecticides, herbicide and rodenticides. The pesticide may be Demeton-S, Demeton-S-methyl, Demeton-S-methylsulphon, Demetonmethyl, Parathion, Phosmet, Carbophenothion, Benoxafos, Azinphos-methyl, Azinphos-ethyl, Amiton, Amidithion, Cyanthoate, Dialiphos, Dimethoate, Dioxathion, Disulfoton, Endothion, Etion, Ethoate-methyl, Formothion, Malathion, Mercarbam, Omethoate, Oxydeprofos, Oxydisulfoton, Phenkapton, Phorate, Phosalone, Prothidathion, Prothoate, Sophamide, Thiometon, Vamidothion, Methamidophos.

In one aspect, the enzymatic activity of a polypeptide of the invention comprises organophosphorous hydrolase activity.

Thus in a first aspect, the present invention relates to isolated polypeptides comprising an amino acid sequence having a degree of identity to the mature polypeptide of SEQ ID NO: 2 of preferably at least 75%, more preferably at least 80%, more preferably at least 85%, even more preferably at least 90%, most preferably at least 95%, and even most preferably at least 96%, at least 97%, at least 98%, or at least 99%, which have organophosphorous hydrolase activity (hereinafter "homologous polypeptides").

In a preferred aspect, the enzymatic activity of a polypeptide of the invention comprises diisopropylfluorophosphatase (DFPase) activity.

Thus in another aspect, the present invention relates to isolated polypeptides comprising an amino acid sequence having a degree of identity to the mature polypeptide of SEQ ID NO: 2 of preferably at least 75%, more preferably at least 80%, more preferably at least 85%, even more preferably at least 90%, most preferably at least 95%, and even most preferably at least 96%, at least 97%, at least 98%, or at least 99%, which have diisopropylfluorophosphatase (DFPase) activity.

In a preferred aspect, the homologous polypeptides have an amino acid sequence that differs by ten amino acids, preferably by five amino acids, more preferably by four amino acids, even more preferably by three amino acids, most preferably by two amino acids, and even most preferably by one amino acid from the mature polypeptide of SEQ ID NO: 2.

A polypeptide of the present invention preferably comprises the amino acid sequence of SEQ ID NO: 2 or an allelic variant thereof; or a fragment thereof having organophosphorous hydrolase activity. In a preferred aspect, the polypeptide comprises the amino acid sequence of SEQ ID NO: 2. In another preferred aspect, the polypeptide comprises the mature polypeptide of SEQ ID NO: 2. In another preferred aspect, the polypeptide consists of the amino acid sequence of SEQ ID NO: 2 or an allelic variant thereof; or a fragment thereof having organophosphorous hydrolase activity. In another preferred aspect, the polypeptide consists of the amino acid sequence of SEQ ID NO: 2. In another preferred aspect, the polypeptide consists of the mature polypeptide of SEQ ID NO: 2.

In a second aspect, the present invention relates to isolated polypeptides having organophosphorous hydrolase activity that are encoded by polynucleotides that hybridize under preferably very low stringency conditions, more preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) a DNA sequence comprising the mature polypeptide coding sequence of SEQ ID NO: 1, (iii) a subsequence of (i) or (ii), or (iv) a full-length complementary strand of (i), (ii), or (iii) (J. Sambrook, E. F. Fritsch, and T. Maniatis, 1989, Molecular Cloning, A Laboratory Manual, 2d edition, Cold Spring Harbor, N.Y.). A subsequence of the mature polypeptide coding sequence of SEQ ID NO: 1 contains at least 100 contiguous nucleotides or preferably at least 200 contiguous nucleotides. Moreover, the subsequence may encode a polypeptide fragment having organophosphorous hydrolase activity. In a preferred aspect, the complementary strand is the full-length complementary strand of the mature polypeptide coding sequence of SEQ ID NO: 1.

The nucleotide sequence of SEQ ID NO: 1; or a subsequence thereof; as well as the amino acid sequence of SEQ ID NO: 2; or a fragment thereof; may be used to design nucleic acid probes to identify and clone DNA encoding polypeptides having organophosphorous hydrolase activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 14, preferably at least 25, more preferably at least 35, and most preferably at least 70 nucleotides in length. It is, however, preferred that the nucleic acid probe is at least 100 nucleotides in length. For example, the nucleic acid probe may be at least 200 nucleotides, preferably at least 300 nucleotides, more preferably at least 400 nucleotides, or most preferably at least 500 nucleotides in length. Even longer probes may be used, e.g., nucleic acid probes that are preferably at least 600 nucleotides, more preferably at least 700 nucleotides, even more preferably at least 800 nucleotides, or most preferably at least 900 nucleotides in length. Both DNA and RNA probes can be used. The probes are typically labeled for detecting the corresponding gene (for example, with $^{32}P$, $^{3}H$, $^{35}S$, biotin, or avidin). Such probes are encompassed by the present invention.

A genomic DNA or cDNA library prepared from such other strains may, therefore, be screened for DNA that hybridizes with the probes described above and encodes a polypeptide having organophosphorous hydrolase activity. Genomic or other DNA from such other strains may be separated by agarose or polyacrylamide gel electrophoresis, or other separation techniques. DNA from the libraries or the separated DNA may be transferred to and immobilized on nitrocellulose or other suitable carrier material. In order to identify a clone or DNA that is homologous with SEQ ID NO: 1; or a subsequence thereof; the carrier material is preferably used in a Southern blot.

For purposes of the present invention, hybridization indicates that the nucleotide sequence hybridizes to a labeled nucleic acid probe corresponding to the mature polypeptide coding sequence of SEQ ID NO: 1; a DNA sequence comprising the mature polypeptide coding sequence of SEQ ID NO: 1; its full-length complementary strand; or a subsequence thereof; under very low to very high stringency conditions. Molecules to which the nucleic acid probe hybridizes under these conditions can be detected using, for example, X-ray film.

In a preferred aspect, the nucleic acid probe is the mature polypeptide coding sequence of SEQ ID NO: 1. In another preferred aspect, the nucleic acid probe is a polynucleotide sequence that encodes the polypeptide of SEQ ID NO: 2, or a subsequence thereof. In another preferred aspect, the nucleic acid probe is SEQ ID NO: 1. In another preferred aspect, the nucleic acid probe is the polynucleotide sequence contained in plasmid NN059104, wherein the polynucleotide sequence thereof encodes a polypeptide having organophosphorous hydrolase activity. In another preferred aspect, the nucleic acid probe is the mature polypeptide coding region contained in plasmid NN059104.

For long probes of at least 100 nucleotides in length, very low to very high stringency conditions are defined as prehybridization and hybridization at 42° C. in 5×SSPE, 0.3% SDS, 200 µg/ml sheared and denatured salmon sperm DNA, and either 25% formamide for very low and low stringencies, 35% formamide for medium and medium-high stringencies, or 50% formamide for high and very high stringencies, following standard Southern blotting procedures for 12 to 24 hours optimally.

For long probes of at least 100 nucleotides in length, the carrier material is finally washed three times each for 15 minutes using 2×SSC, 0.2% SDS preferably at 55° C. (medium stringency), more preferably at 60° C. (medium-high stringency), even more preferably at 65° C. (high stringency), and most preferably at 70° C. (very high stringency).

For short probes that are about 15 nucleotides to about 70 nucleotides in length, stringency conditions are defined as prehybridization, hybridization, and washing post-hybridization at about 5° C. to about 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures for 12 to 24 hours optimally.

For short probes that are about 15 nucleotides to about 70 nucleotides in length, the carrier material is washed once in 6×SCC plus 0.1% SDS for 15 minutes and twice each for 15 minutes using 6×SSC at 5° C. to 10° C. below the calculated $T_m$.

In a third aspect, the present invention relates to isolated polypeptides having organophosphorous hydrolase activity encoded by polynucleotides comprising or consisting of nucleotide sequences that have a degree of identity to the mature polypeptide coding sequence of SEQ ID NO: 1 of preferably at least 75%, more preferably at least 80%, more preferably at least 85%, even more preferably at least 90%, most preferably at least 95%, and even most preferably 96%, 97%, 98%, or 99%, which encode an active polypeptide. See polynucleotide section herein.

In a fourth aspect, the present invention relates to artificial variants comprising a substitution, deletion, and/or insertion of one or more (or several) amino acids of the mature polypeptide of SEQ ID NO: 2; or a homologous sequence thereof. Preferably, amino acid changes are of a minor nature, that is conservative amino acid substitutions or insertions that do not significantly affect the folding and/or activity of the protein; small deletions, typically of one to about 30 amino acids; small amino- or carboxyl-terminal extensions, such as an amino-terminal methionine residue; a small linker peptide of up to about 20-25 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions that do not generally alter specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly.

In addition to the 20 standard amino acids, non-standard amino acids (such as 4-hydroxyproline, 6-N-methyl lysine, 2-aminoisobutyric acid, isovaline, and alpha-methyl serine) may be substituted for amino acid residues of a wild-type polypeptide. A limited number of non-conservative amino acids, amino acids that are not encoded by the genetic code, and unnatural amino acids may be substituted for amino acid residues. "Unnatural amino acids" have been modified after protein synthesis, and/or have a chemical structure in their side chain(s) different from that of the standard amino acids. Unnatural amino acids can be chemically synthesized, and preferably, are commercially available, and include pipecolic acid, thiazolidine carboxylic acid, dehydroproline, 3- and 4-methylproline, and 3,3-dimethylproline.

Alternatively, the amino acid changes are of such a nature that the physico-chemical properties of the polypeptides are altered. For example, amino acid changes may improve the thermal stability of the polypeptide, alter the substrate specificity, change the pH optimum, and the like.

Essential amino acids in the parent polypeptide can be identified according to procedures known in the art, such as site-directed mutagenesis or alanine-scanning mutagenesis (Cunningham and Wells, 1989, *Science* 244: 1081-1085). In the latter technique, single alanine mutations are introduced at every residue in the molecule, and the resultant mutant molecules are tested for biological activity (i.e., organophosphorous hydrolase activity) to identify amino acid residues that are critical to the activity of the molecule. See also, Hilton et al., 1996, *J. Biol. Chem.* 271: 4699-4708. The active site of the enzyme or other biological interaction can also be determined by physical analysis of structure, as determined by such techniques as nuclear magnetic resonance, crystallography, electron diffraction, or photoaffinity labeling, in conjunction with mutation of putative contact site amino acids. See, for example, de Vos et al., 1992, *Science* 255: 306-312; Smith et al., 1992, *J. Mol. Biol.* 224: 899-904; Wlodaver et al., 1992, *FEBS Lett.* 309: 59-64. The identities of essential amino acids can also be inferred from analysis of identities with polypeptides that are related to a polypeptide according to the invention.

Single or multiple amino acid substitutions, deletions, and/or insertions can be made and tested using known methods of mutagenesis, recombination, and/or shuffling, followed by a relevant screening procedure, such as those disclosed by Reidhaar-Olson and Sauer, 1988, *Science* 241: 53-57; Bowie and Sauer, 1989, *Proc. Natl. Acad. Sci. USA* 86: 2152-2156; WO 95/17413; or WO 95/22625. Other methods that can be used include error-prone PCR, phage display (e.g., Lowman et al., 1991, *Biochem.* 30: 10832-10837; U.S. Pat. No. 5,223,409; WO 92/06204), and region-directed mutagenesis (Derbyshire et al., 1986, *Gene* 46: 145; Ner et al., 1988, DNA 7: 127).

Mutagenesis/shuffling methods can be combined with high-throughput, automated screening methods to detect activity of cloned, mutagenized polypeptides expressed by host cells (Ness et al., 1999, *Nature Biotechnology* 17: 893-896). Mutagenized DNA molecules that encode active polypeptides can be recovered from the host cells and rapidly sequenced using standard methods in the art. These methods allow the rapid determination of the importance of individual amino acid residues in a polypeptide of interest, and can be applied to polypeptides of unknown structure.

The total number of amino acid substitutions, deletions and/or insertions of the mature polypeptide of SEQ ID NO: 2, may be at least 40, preferably at least 35, preferably at least 30, preferably at least 25, preferably at least 20, preferably at least 15, preferably at least 10, preferably at least 9, preferably at least 8, preferably at least 7, preferably at least 6, preferably at least 5, preferably at least 4, preferably at least 3, preferably at least 2 or preferably at least 1.

Sources of Polypeptides Having Organophosphorous Hydrolase Activity

A polypeptide of the present invention may be obtained from marine organisms of any genus. For purposes of the present invention, the term "obtained from" as used herein in connection with a given source shall mean that the polypeptide encoded by a nucleotide sequence is produced by the source or by a strain in which the nucleotide sequence from the source has been inserted. In a preferred aspect, the polypeptide obtained from a given source is secreted extracellularly.

A polypeptide having organophosphorous hydrolase activity of the present invention may be a bacterial polypeptide. For example, the polypeptide may be a gram positive bacterial polypeptide such as a *Bacillus, Streptococcus, Streptomyces, Staphylococcus, Enterococcus, Lactobacillus, Lactococcus, Clostridium, Geobacillus,* or *Oceanobacillus* polypeptide having organophosphorous hydrolase activity, or a Gram negative bacterial polypeptide such as an *E. coli, Pseudomonas, Salmonella, Campylobacter, Helicobacter, Flavobacterium, Fusobacterium, Ilyobacter, Neisseria,* or *Ureaplasma* polypeptide having organophosphorous hydrolase activity.

In a preferred aspect, the polypeptide is a *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis* polypeptide having organophosphorous hydrolase activity.

In another preferred aspect, the polypeptide is a *Streptococcus equisimilis, Streptococcus pyogenes, Streptococcus uberis,* or *Streptococcus equi* subsp. *Zooepidemicus* polypeptide having organophosphorous hydrolase activity.

In another preferred aspect, the polypeptide is a *Streptomyces achromogenes, Streptomyces avermitilis, Streptomyces coelicolor, Streptomyces griseus,* or *Streptomyces lividans* polypeptide having organophosphorous hydrolase activity.

A polypeptide having organophosphorous hydrolase activity of the present invention may also be a fungal polypeptide, and more preferably a yeast polypeptide such as a *Candida, Kluyveromyces, Pichia, Saccharomyces, Schizosaccharomyces,* or *Yarrowia* polypeptide having organophosphorous hydrolase activity; or more preferably a filamentous fungal polypeptide such as an *Acremonium, Agaricus, Alternaria, Aspergillus, Aureobasidium, Botryospaeria, Ceriporiopsis, Chaetomidium, Chrysosporium, Claviceps, Cochliobolus, Coprinopsis, Coptotermes, Corynascus, Cryphonectria, Cryptococcus, Diplodia, Exidia, Filibasidium, Fusarium, Gibberella, Holomastigotoides, Humicola, Irpex, Lentinula, Leptospaeria, Magnaporthe, Melanocarpus, Meripilus, Mucor, Myceliophthora, Neocallimastix, Neurospora, Paecilomyces, Penicillium, Phanerochaete, Piromyces, Poitrasia, Pseudoplectania, Pseudotrichonympha, Rhizomucor, Schizophyllum, Scytalidium, Talaromyces, Thermoascus, Thielavia, Tolypocladium, Trichoderma, Trichophaea, Verticillium, Volvariella,* or *Xylaria* polypeptide having organophosphorous hydrolase activity.

In a preferred aspect, the polypeptide is a *Saccharomyces carlsbergensis, Saccharomyces cerevisiae, Saccharomyces diastaticus, Saccharomyces douglasfi, Saccharomyces kluyveri, Saccharomyces norbensis,* or *Saccharomyces oviformis* polypeptide having organophosphorous hydrolase activity.

In another preferred aspect, the polypeptide is an *Acremonium cellulolyticus, Aspergillus aculeatus, Aspergillus awamori, Aspergillus fumigatus, Aspergillus foetidus, Aspergillus japonicus, Aspergillus nidulans, Aspergillus niger, Aspergillus oryzae, Chrysosporium keratinophilum, Chrysosporium lucknowense, Chrysosporium tropicum, Chrysosporium merdarium, Chrysosporium inops, Chrysosporium pannicola, Chrysosporium queenslandicum, Chrysosporium zonaturn, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sporotrichioides, Fusarium sulphureum, Fusarium torulosum, Fusarium trichothecioides, Fusarium venenatum, Humicola grisea, Humicola insolens, Humicola lanuginosa, Irpex lacteus, Mucor miehei, Myceliophthora thermophila, Neurospora crassa, Penicillium funiculosum, Penicillium purpurogenum, Phanerochaete chrysosporium, Thielavia achromatica, Thielavia albomyces, Thielavia albopilosa, Thielavia australeinsis, Thielavia fimeti, Thielavia microspora, Thielavia ovispora, Thielavia peruviana, Thielavia spededonium, Thielavia setosa, Thielavia subthermophila, Thielavia terrestris, Trichoderma harzianum, Trichoderma koningii, Trichoderma longibrachiatum, Trichoderma reesei,* or *Trichoderma viride* polypeptide having having organophosphorous hydrolase activity.

In one aspect of the invention the polypeptide is from marine animals, such as cephalopods and mollusks. In a preferred aspect, the polypeptide is an *Aplysia californica* polypeptide. In a more preferred aspect, the polypeptide is an *Aplysia californica* polypeptide having organophosphorous hydrolase activity. In a most preferred aspect, the polypeptide is an *Aplysia californica* Deposit No DSM 22525 polypeptide having organophosphorous hydrolase activity, e.g., the polypeptide comprising the mature polypeptide of SEQ ID NO: 2 *Escherichia coli* NN059104.

It will be understood that for the aforementioned species the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen and Zellkulturen GmbH (DSM), Centraalbureau Voor Schimmelcultures (CBS), and Agricultural Research Service Patent Culture Collection, Northern Regional Research Center (NRRL) and NCIMB.

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The polynucleotide may then be obtained by similarly screening a genomic or cDNA library of such a microorganism. Once a polynucleotide sequence encoding a polypeptide has been detected with the probe(s), the polynucleotide can be isolated or cloned by utilizing techniques that are well known to those of ordinary skill in the art (see, e.g., Sambrook et al., 1989, supra).

Polypeptides of the present invention also include fused polypeptides or cleavable fusion polypeptides in which another polypeptide is fused at the N-terminus or the C-terminus of the polypeptide or fragment thereof. A fused polypeptide is produced by fusing a nucleotide sequence (or a portion thereof) encoding another polypeptide to a nucleotide sequence (or a portion thereof) of the present invention. Techniques for producing fusion polypeptides are known in the art, and include ligating the coding sequences encoding the polypeptides so that they are in frame and that expression of the fused polypeptide is under control of the same promoter(s) and terminator.

A fusion polypeptide can further comprise a cleavage site. Upon secretion of the fusion protein, the site is cleaved releasing the polypeptide having organophosphorous hydrolase activity from the fusion protein. Examples of cleavage sites include, but are not limited to, a Kex2 site that encodes the dipeptide Lys-Arg (Martin et al., 2003, *J. Ind. Microbiol. Biotechnol.* 3: 568-76; Svetina et al., 2000, *J. Biotechnol.* 76: 245-251; Rasmussen-Wilson et al., 1997, *Appl. Environ. Microbiol.* 63: 3488-3493; Ward et al., 1995, *Biotechnology* 13: 498-503; and Contreras et al., 1991, *Biotechnology* 9: 378-381), an Ile-(Glu or Asp)-Gly-Arg site, which is cleaved by a Factor Xa protease after the arginine residue (Eaton et al., 1986, *Biochem.* 25: 505-512); a Asp-Asp-Asp-Asp-Lys site, which is cleaved by an enterokinase after the lysine (Collins-Racie et al., 1995, *Biotechnology* 13: 982-987); a His-Tyr-Glu site or His-Tyr-Asp site, which is cleaved by Genenase I (Carter et al., 1989, *Proteins: Structure, Function, and Genetics* 6: 240-248); a Leu-Val-Pro-Arg-Gly-Ser site, which is cleaved by thrombin after the Arg (Stevens, 2003, *Drug Discovery World* 4: 35-48); a Glu-Asn-Leu-Tyr-Phe-Gln-Gly site, which is cleaved by TEV protease after the Gln (Stevens, 2003, supra); and a Leu-Glu-Val-Leu-Phe-Gln-Gly-Pro site, which is cleaved by a genetically engineered form of human rhinovirus 3C protease after the Gln (Stevens, 2003, supra).

Polynucleotides

The present invention also relates to isolated polynucleotides comprising or consisting of nucleotide sequences that encode polypeptides having organophosphorous hydrolase activity of the present invention.

In a preferred aspect, the nucleotide sequence comprises or consists of SEQ ID NO: 1.

In another more preferred aspect, the nucleotide sequence comprises or consists of the sequence contained in plasmid NN059104 which is contained in *E. coli* Top10. In another preferred aspect, the nucleotide sequence comprises or consists of the mature polypeptide coding sequence of SEQ ID NO: 1. In another more preferred aspect, the nucleotide sequence comprises or consists of the mature polypeptide coding sequence contained in plasmid NN059104 which is contained in *E. coli* Top10. The present invention also encompasses nucleotide sequences that encode polypeptides comprising or consisting of the amino acid sequence of SEQ ID NO: 2 or the mature polypeptide thereof, which differ from SEQ ID NO: 1 or the mature polypeptide coding sequence thereof by virtue of the degeneracy of the genetic code. The present invention also relates to subsequences of SEQ ID NO: 1 that encode fragments of SEQ ID NO: 2 that have organophosphorous hydrolase activity.

The present invention also relates to mutant polynucleotides comprising or consisting of at least one mutation in the mature polypeptide coding sequence of SEQ ID NO: 1, in which the mutant nucleotide sequence encodes the mature polypeptide of SEQ ID NO: 2.

The techniques used to isolate or clone a polynucleotide encoding a polypeptide are known in the art and include isolation from genomic DNA, preparation from cDNA, or a combination thereof. The cloning of the polynucleotides of the present invention from such DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleotide sequence-based amplification (NASBA) may be used. The polynucleotides may be cloned from an *Aplysia californica*, or another or related organism and thus, for example, may be an allelic or species variant of the polypeptide encoding region of the nucleotide sequence.

The present invention also relates to isolated polynucleotides comprising or consisting of nucleotide sequences that have a degree of identity to the mature polypeptide coding sequence of SEQ ID NO: 1 of at least 65%, more preferably at least 70%, more preferably at least 75%, more preferably at least 80%, more preferably at least 85%, even more preferably at least 90%, most preferably at least 95%, and even most preferably at least 96%, at least 97%, at least 98%, or at least 99% identity, which encode an active polypeptide.

Modification of a nucleotide sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., artificial variants that differ in specific activity, thermostability, pH optimum, or the like. The variant sequence may be constructed on the basis of the nucleotide sequence presented as the mature polypeptide coding sequence of SEQ ID NO: 1, e.g., a subsequence thereof, and/or by introduction of nucleotide substitutions that do not give rise to another amino acid sequence of the polypeptide encoded by the nucleotide sequence, but which correspond to the codon usage of the host organism intended for production of the enzyme, or by introduction of nucleotide substitutions that may give rise to a different amino acid sequence. For a general description of nucleotide substitution, see, e.g., Ford et al., 1991, *Protein Expression and Purification* 2: 95-107.

It will be apparent to those skilled in the art that such substitutions can be made outside the regions critical to the function of the molecule and still result in an active polypeptide. Amino acid residues essential to the activity of the polypeptide encoded by an isolated polynucleotide of the invention, and therefore preferably not subject to substitution, may be identified according to procedures known in the art, such as site-directed mutagenesis or alanine-scanning mutagenesis (see, e.g., Cunningham and Wells, 1989, supra). In the latter technique, mutations are introduced at every positively charged residue in the molecule, and the resultant mutant molecules are tested for organophosphorous hydrolase activity to identify amino acid residues that are critical to the activity of the molecule. Sites of substrate-enzyme interaction can also be determined by analysis of the three-dimensional structure as determined by such techniques as nuclear magnetic resonance analysis, crystallography or photoaffinity labeling (see, e.g., de Vos et al., 1992, supra; Smith et al., 1992, supra; Wlodaver et al., 1992, supra).

The present invention also relates to isolated polynucleotides encoding polypeptides of the present invention, which hybridize under very low stringency conditions, preferably low stringency conditions, more preferably medium stringency conditions, more preferably medium-high stringency conditions, even more preferably high stringency conditions, and most preferably very high stringency conditions with (i) the mature polypeptide coding sequence of SEQ ID NO: 1, (ii) a DNA sequence comprising the mature polypeptide coding sequence of SEQ ID NO: 1, or (iii) a full-length complementary strand of (i) or (ii); or allelic variants and subsequences thereof (Sambrook et al., 1989, supra), as defined herein. In a preferred aspect, the complementary strand is the full-length complementary strand of the mature polypeptide coding sequence of SEQ ID NO: 1.

The present invention also relates to isolated polynucleotides obtained by (a) hybridizing a population of DNA under very low, low, medium, medium-high, high, or very high stringency conditions with (i) the mature polypeptide coding sequence of SEQ ID NO: 1, (ii) a DNA sequence comprising the mature polypeptide coding sequence of SEQ ID NO: 1, or (iii) a full-length complementary strand of (i) or (ii); and (b) isolating the hybridizing polynucleotide, which encodes a polypeptide having organophosphorous hydrolase activity. In a preferred aspect, the complementary strand is the full-length complementary strand of the mature polypeptide coding sequence of SEQ ID NO: 1.

Nucleic Acid Constructs

The present invention also relates to nucleic acid constructs comprising an isolated polynucleotide of the present invention operably linked to one or more (several) control sequences that direct the expression of the coding sequence in a suitable host cell under conditions compatible with the control sequences.

An isolated polynucleotide encoding a polypeptide of the present invention may be manipulated in a variety of ways to provide for expression of the polypeptide. Manipulation of the polynucleotide's sequence prior to its insertion into a vector may be desirable or necessary depending on the expression vector. The techniques for modifying polynucleotide sequences utilizing recombinant DNA methods are well known in the art.

The control sequence may be an appropriate promoter sequence, a nucleotide sequence that is recognized by a host cell for expression of a polynucleotide encoding a polypeptide of the present invention. The promoter sequence contains transcriptional control sequences that mediate the expression of the polypeptide. The promoter may be any nucleotide sequence that shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, *Proceedings of the National Academy of Sciences USA* 75: 3727-3731), as well as the tac promoter (DeBoer et al., 1983, *Proceedings of the National Academy of Sciences USA* 80: 21-25). Further promoters are described in "Useful proteins from recombinant bacteria" in *Scientific American*, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, *Fusarium venenatum* amyloglucosidase (WO 00/56900), *Fusarium venenatum* Daria (WO 00/56900), *Fusarium venenatum* Quinn (WO 00/56900), *Fusarium oxysporum* trypsin-like protease (WO 96/00787), *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase III, *Trichoderma reesei* endoglucanase IV, *Trichoderma reesei* endoglucanase V, *Trichoderma reesei* xylanase I, *Trichoderma reesei* xylanase II, *Trichoderma reesei* beta-xylosidase, as well as the NA2-tpi promoter (a hybrid of the promoters from the genes for *Aspergillus niger* neutral alpha-amylase and *Aspergillus oryzae* triose phosphate isomerase); and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase. Other useful promoters for yeast host cells are described by Romanos et al., 1992, *Yeast* 8: 423-488.

The control sequence may also be a suitable transcription terminator sequence, a sequence recognized by a host cell to terminate transcription. The terminator sequence is operably linked to the 3' terminus of the nucleotide sequence encoding the polypeptide. Any terminator that is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C(CYC1), and *Saccharomyces*

*cerevisiae* glyceraldehyde-3-phosphate dehydrogenase. Other useful terminators for yeast host cells are described by Romanos et al., 1992, supra.

The control sequence may also be a suitable leader sequence, a nontranslated region of an mRNA that is important for translation by the host cell. The leader sequence is operably linked to the 5' terminus of the nucleotide sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleotide sequence and, when transcribed, is recognized by the host cell as a signal to add polyadenosine residues to transcribed mRNA. Any polyadenylation sequence that is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, *Molecular Cellular Biology* 15: 5983-5990.

The control sequence may also be a signal peptide coding sequence that codes for an amino acid sequence linked to the amino terminus of a polypeptide and directs the encoded polypeptide into the cell's secretory pathway. The 5' end of the coding sequence of the nucleotide sequence may inherently contain a signal peptide coding sequence naturally linked in translation reading frame with the segment of the coding sequence that encodes the secreted polypeptide. Alternatively, the 5' end of the coding sequence may contain a signal peptide coding sequence that is foreign to the coding sequence. The foreign signal peptide coding sequence may be required where the coding sequence does not naturally contain a signal peptide coding sequence. Alternatively, the foreign signal peptide coding sequence may simply replace the natural signal peptide coding sequence in order to enhance secretion of the polypeptide. However, any signal peptide coding sequence that directs the expressed polypeptide into the secretory pathway of a host cell of choice, i.e., secreted into a culture medium, may be used in the present invention.

Effective signal peptide coding sequences for bacterial host cells are the signal peptide coding sequences obtained from the genes for *Bacillus* NCIB 11837 maltogenic amylase, *Bacillus stearothermophilus* alpha-amylase, *Bacillus licheniformis* subtilisin, *Bacillus licheniformis* beta-lactamase, *Bacillus stearothermophilus* neutral proteases (nprT, nprS, nprM), *Bacillus clausii* alcaline protease (aprH) and *Bacillus subtilis* prsA. Further signal peptides are described by Simonen and Palva, 1993, *Microbiological Reviews* 57: 109-137.

Effective signal peptide coding sequences for filamentous fungal host cells are the signal peptide coding sequences obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, *Humicola insolens* endoglucanase V, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding sequences are described by Romanos et al., 1992, supra.

In one aspect, the isolated, synthetic or recombinant polypeptide can comprise the polypeptide of the invention that lacks a signal sequence.

The control sequence may also be a propeptide coding sequence that codes for an amino acid sequence positioned at the amino terminus of a polypeptide. The resultant polypeptide is known as a proenzyme or propolypeptide (or a zymogen in some cases). A propeptide is generally inactive and can be converted to a mature active polypeptide by catalytic or autocatalytic cleavage of the propeptide from the propolypeptide. The propeptide coding sequence may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide sequences are present at the amino terminus of a polypeptide, the propeptide sequence is positioned next to the amino terminus of a polypeptide and the signal peptide sequence is positioned next to the amino terminus of the propeptide sequence.

It may also be desirable to add regulatory sequences that allow the regulation of the expression of the polypeptide relative to the growth of the host cell. Examples of regulatory systems are those that cause the expression of the gene to be turned on or off in response to a chemical or physical stimulus, including the presence of a regulatory compound. Regulatory systems in prokaryotic systems include the lac, tac, xyl and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the nucleotide sequence encoding the polypeptide would be operably linked with the regulatory sequence.

Expression Vectors

The present invention also relates to recombinant expression vectors comprising a polynucleotide of the present invention, a promoter, and transcriptional and translational stop signals. The various nucleic acids and control sequences described herein may be joined together to produce a recombinant expression vector that may include one or more (several) convenient restriction sites to allow for insertion or substitution of the nucleotide sequence encoding the polypeptide at such sites. Alternatively, a polynucleotide sequence of the present invention may be expressed by inserting the nucleotide sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the nucleotide sequence. The choice of the vector will typically depend on the compatibility of the vector with the host cell into which the vector is to be introduced. The vectors may be linear or closed circular plasmids.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vectors of the present invention preferably contain one or more (several) selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are the dal genes from *Bacillus subtilis* or *Bacillus licheniformis*, or markers that confer antibiotic resistance such as ampicillin, kanamycin, chloramphenicol, or tetracycline resistance. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or nonhomologous recombination. Alternatively, the vector may contain additional nucleotide sequences for directing integration by homologous recombination into the genome of the host cell at a precise location(s) in the chromosome(s). To increase the likelihood of integration at a precise location, the integrational elements should preferably contain a sufficient number of nucleic acids, such as 100 to 10,000 base pairs, preferably 400 to 10,000 base pairs, and most preferably 800 to 10,000 base pairs, which have a high degree of identity to the corresponding target sequence to enhance the probability of homologous recombination. The integrational elements may be any sequence that is homologous with the target sequence in the genome of the host cell. Furthermore, the integrational elements may be non-encoding or encoding nucleotide sequences. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" is defined herein as a nucleotide sequence that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMR1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1 (Gems et al., 1991, *Gene* 98: 61-67; Cullen et al., 1987, *Nucleic Acids Research* 15: 9163-9175; WO 00/24883). Isolation of the AMA1 gene and construction of plasmids or vectors comprising the gene can be accomplished according to the methods disclosed in WO 00/24883.

More than one copy of a polynucleotide of the present invention may be inserted into a host cell to increase production of the gene product. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

Host Cells

The present invention also relates to recombinant host cells, comprising an isolated polynucleotide of the present invention, which are advantageously used in the recombinant production of the polypeptides. A vector comprising a polynucleotide of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram positive bacterium or a Gram negative bacterium. Gram positive bacteria include, but not limited to, *Bacillus, Streptococcus, Streptomyces, Staphylococcus, Enterococcus, Lactobacillus, Lactococcus, Clostridium, Geobacillus*, and *Oceanobacillus*. Gram negative bacteria include, but not limited to, *E. coli, Pseudomonas, Salmonella, Campylobacter, Helicobacter, Flavobacterium, Fusobacterium, Ilyobacter, Neisseria*, and *Ureaplasma*.

The bacterial host cell may be any *Bacillus* cell. *Bacillus* cells useful in the practice of the present invention include, but are not limited to, *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis*, and *Bacillus thuringiensis* cells.

In a preferred aspect, the bacterial host cell is a *Bacillus amyloliquefaciens*, *Bacillus lentus*, *Bacillus licheniformis*, *Bacillus stearothermophilus* or *Bacillus subtilis* cell. In a more preferred aspect, the bacterial host cell is a *Bacillus amyloliquefaciens* cell. In another more preferred aspect, the bacterial host cell is a *Bacillus clausii* cell. In another more preferred aspect, the bacterial host cell is a *Bacillus licheniformis* cell. In another more preferred aspect, the bacterial host cell is a *Bacillus subtilis* cell.

The bacterial host cell may also be any *Streptococcus* cell. *Streptococcus* cells useful in the practice of the present invention include, but are not limited to, *Streptococcus equisimilis*, *Streptococcus pyogenes*, *Streptococcus uberis*, and *Streptococcus equi* subsp. *Zooepidemicus* cells.

In a preferred aspect, the bacterial host cell is a *Streptococcus equisimilis* cell. In another preferred aspect, the bacterial host cell is a *Streptococcus pyogenes* cell. In another preferred aspect, the bacterial host cell is a *Streptococcus uberis* cell. In another preferred aspect, the bacterial host cell is a *Streptococcus equi* subsp. *Zooepidemicus* cell.

The bacterial host cell may also be any *Streptomyces* cell. *Streptomyces* cells useful in the practice of the present invention include, but are not limited to, *Streptomyces achromogenes*, *Streptomyces avermitilis*, *Streptomyces coelicolor*, *Streptomyces griseus*, and *Streptomyces lividans* cells.

In a preferred aspect, the bacterial host cell is a *Streptomyces achromogenes* cell. In another preferred aspect, the bacterial host cell is a *Streptomyces avermitilis* cell. In another preferred aspect, the bacterial host cell is a *Streptomyces coelicolor* cell. In another preferred aspect, the bacterial host cell is a *Streptomyces griseus* cell. In another preferred aspect, the bacterial host cell is a *Streptomyces lividans* cell.

The introduction of DNA into a *Bacillus* cell may, for instance, be effected by protoplast transformation (see, e.g., Chang and Cohen, 1979, *Molecular General Genetics* 168: 111-115), by using competent cells (see, e.g., Young and Spizizen, 1961, *Journal of Bacteriology* 81: 823-829, or Dubnau and Davidoff-Abelson, 1971, *Journal of Molecular Biology* 56: 209-221), by electroporation (see, e.g., Shigekawa and Dower, 1988, *Biotechniques* 6: 742-751), or by conjugation (see, e.g., Koehler and Thorne, 1987, *Journal of Bacteriology* 169: 5271-5278). The introduction of DNA into an *E. coli* cell may, for instance, be effected by protoplast transformation (see, e.g., Hanahan, 1983, *J. Mol. Biol.* 166: 557-580) or electroporation (see, e.g., Dower et al., 1988, *Nucleic Acids Res.* 16: 6127-6145). The introduction of DNA into a *Streptomyces* cell may, for instance, be effected by protoplast transformation and electroporation (see, e.g., Gong et al., 2004, *Folia Microbiol.* (Praha) 49: 399-405), by conjugation (see, e.g., Mazodier et al., 1989, *J. Bacteriol.* 171: 3583-3585), or by transduction (see, e.g., Burke et al., 2001, *Proc. Natl. Acad. Sci. USA* 98: 6289-6294). The introduction of DNA into a *Pseudomonas* cell may, for instance, be effected by electroporation (see, e.g., Choi et al., 2006, *J. Microbiol. Methods* 64: 391-397) or by conjugation (see, e.g., Pinedo and Smets, 2005, *Appl. Environ. Microbiol.* 71: 51-57). The introduction of DNA into a *Streptococcus* cell may, for instance, be effected by natural competence (see, e.g., Perry and Kuramitsu, 1981, *Infect. Immun.* 32: 1295-1297), by protoplast transformation (see, e.g., Catt and Jollick, 1991, *Microbios.* 68: 189-2070, by electroporation (see, e.g., Buckley et al., 1999, *Appl. Environ. Microbiol.* 65: 3800-3804) or by conjugation (see, e.g., Clewell, 1981, *Microbiol. Rev.* 45: 409-436). However, any method known in the art for introducing DNA into a host cell can be used.

The host cell may also be a eukaryote, such as a mammalian, insect, plant, or fungal cell.

In a preferred aspect, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi*, 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In a more preferred aspect, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

In an even more preferred aspect, the yeast host cell is a *Candida*, *Hansenula*, *Kluyveromyces*, *Pichia*, *Saccharomyces*, *Schizosaccharomyces*, or *Yarrowia* cell. Further yeast host cells are described in WO2007/023163, page 23, lines 1-15.

In another more preferred aspect, the fungal host cell is a filamentous fungal cell. "Filamentous fungi" include all filamentous forms of the subdivision Eumycota and Oomycota (as defined by Hawksworth et al., 1995, supra). The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

In an even more preferred aspect, the filamentous fungal host cell is an *Acremonium*, *Aspergillus*, *Aureobasidium*, *Bjerkandera*, *Ceriporiopsis*, *Chrysosporium*, *Coprinus*, *Coriolus*, *Cryptococcus*, *Filibasidium*, *Fusarium*, *Humicola*, *Magnaporthe*, *Mucor*, *Myceliophthora*, *Neocallimastix*, *Neurospora*, *Paecilomyces*, *Penicillium*, *Phanerochaete*, *Phlebia*, *Piromyces*, *Pleurotus*, *Schizophyllum*, *Talaromyces*, *Thermoascus*, *Thielavia*, *Tolypocladium*, *Trametes*, or *Trichoderma* cell. Further filamentous host cells are described in WO2007/023163, page 23 lines 20-35.

Fungal cells may be transformed by a process involving protoplast formation, transformation of the protoplasts, and regeneration of the cell wall in a manner known per se. Suitable procedures for transformation of *Aspergillus* and *Trichoderma* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156, and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

Methods of Production

The present invention also relates to methods of producing a polypeptide of the present invention, comprising: (a) cultivating a cell, which in its wild-type form produces the polypeptide, under conditions conducive for production of the polypeptide; and (b) recovering the polypeptide. In a preferred aspect, the cell is of the genus *Aplysia*. In a most preferred aspect, the cell is *Aplysia californica* DSM 22525.

The present invention also relates to methods of producing a polypeptide of the present invention, comprising: (a) cultivating a recombinant host cell, as described herein, under conditions conducive for production of the polypeptide; and (b) recovering the polypeptide.

The present invention also relates to methods of producing a polypeptide of the present invention, comprising: (a) cultivating a recombinant host cell under conditions conducive for production of the polypeptide, wherein the host cell comprises a mutant nucleotide sequence having at least one mutation in the mature polypeptide coding sequence of SEQ ID NO: 1, wherein the mutant nucleotide sequence encodes a polypeptide that comprises or consists of the mature polypeptide of SEQ ID NO: 2, and (b) recovering the polypeptide.

In the production methods of the present invention, the cells are cultivated in a nutrient medium suitable for production of the polypeptide using methods well known in the art. For example, the cell may be cultivated by shake flask cultivation, and small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection). If the polypeptide is secreted into the nutrient medium, the polypeptide can be recovered directly from the medium. If the polypeptide is not secreted into the medium, it can be recovered from cell lysates.

The polypeptides may be detected using methods known in the art that are specific for the polypeptides. These detection methods may include use of specific antibodies, formation of an enzyme product, or disappearance of an enzyme substrate. For example, an enzyme assay may be used to determine the activity of the polypeptide as described herein.

The resulting polypeptide may be recovered using methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., *Protein Purification*, J.-C. Janson and Lars Ryden, editors, VCH Publishers, New York, 1989) to obtain substantially pure polypeptides.

Compositions

The present invention also relates to compositions comprising a polypeptide of the present invention. Preferably, the compositions are enriched in such a polypeptide. The term "enriched" indicates that the organophosphorous hydrolase activity of the composition has been increased, e.g., with an enrichment factor of at least 1.1.

The composition may comprise a polypeptide of the present invention as the major enzymatic component, e.g., a mono-component composition. Alternatively, the composition may comprise multiple enzymatic activities, such as an aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidase, pectinolytic enzyme, peptidoglutaminase, peroxidase, phytase, polyphenoloxidase, proteolytic enzyme, ribonuclease, transglutaminase, or xylanase. The additional enzyme(s) may be produced, for example, by a marine organism or by a microorganism belonging to the genus *Aspergillus*, preferably *Aspergillus aculeatus, Aspergillus awamori, Aspergillus fumigatus, Aspergillus foetidus, Aspergillus japonicus, Aspergillus nidulans, Aspergillus niger,* or *Aspergillus oryzae; Fusarium,* preferably *Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium sulphureum, Fusarium toruloseum, Fusarium trichothecioides,* or *Fusarium venenatum; Humicola,* preferably *Humicola insolens* or *Humicola lanuginosa;* or *Trichoderma,* preferably *Trichoderma harzianum, Trichoderma koningii, Trichoderma longibrachiatum, Trichoderma reesei,* or *Trichoderma viride*.

Alternatively, the enzyme(s) may be produced by microorganism belonging to the genus *Bacillus, Streptococcus, Streptomyces, Staphylococcus, Enterococcus, Lactobacillus, Lactococcus, Clostridium, Geobacillus,* or *Oceanobacillus* or bacteria such as *E. coli, Pseudomonas, Salmonella, Campylobacter, Helicobacter, Flavobacterium, Fusobacterium, Ilyobacter, Neisseria,* or *Ureaplasma*.

The additional enzyme may also be produced by *Bacillus alkalophilus, Bacillus amyloliquefaciens, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus pumilus, Bacillus stearothermophilus, Bacillus subtilis,* or *Bacillus thuringiensis*.

In one aspect the additional enzyme(s) is produced by *Streptococcus equisimilis, Streptococcus pyogenes, Streptococcus uberis,* or *Streptococcus equi*.

In one aspect the additional enzyme(s) is produced by *Streptomyces achromogenes, Streptomyces avermitilis, Streptomyces coelicolor, Streptomyces griseus,* or *Streptomyces lividans*.

The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art.

Examples are given below of preferred uses of the polypeptide compositions of the invention. The dosage of the polypeptide composition of the invention and other conditions under which the composition is used may be determined on the basis of methods known in the art.

Uses

The present invention is also directed to methods for using the polypeptides having organophosphorous hydrolase activity (organophosphorous hydrolases), or compositions thereof.

In one preferred embodiment the invention also directed to the use of organophosphorous hydrolases of the invention for decontaminating an area or a device contaminated with at least one harmful or undesired organophosphorous compound. The organophosphorous hydrolases of the invention or a composition comprising the organophosphorous hydrolases of the invention is applied to the area or the device in an amount sufficient to degrade at least part of the at least one harmful or undesired organophosphorous compound.

In another embodiment the organophosphorous hydrolases of the invention may be used in lotions or other emulsions such as micro emulsions for applying to the skin of e.g. a human. The organophosphorous hydrolases of the invention or a composition comprising the organophosphorous hydrolases of the invention is applied to the skin to protect against at least one harmful or undesired organophosphorous compound.

In a further embodiment the organophosphorous hydrolases of the invention may be incorporated in an assay for detection of at least one harmful or undesired organophosphorous compound. Such assays could be beneficial for quick assessment of the presence of undesired organophosphorous compounds.

Harmful or undesired organophosphorous compounds includes toxic organophosphorous cholinesterase-inhibiting compounds including nerve gases such as diisopropylfluorophosphate (DFP), O-isopropyl methylphosphonofluoridate (sarin), O-pinacolyl methyl phosphonofluoridate (soman) and O-cyclohexyl methylphosphonofluoridate.

Other harmful compounds include V agents, which may comprise VX, VE, VG, VM, VR Tetriso and Soviet V-gas (Russian VX).

The pesticides may comprise fungicides, insecticides, herbicide and rodenticides. The pesticide may be Demeton-S, Demeton-S-methyl, Demeton-S-methylsulphon, Demetonmethyl, Parathion, Phosmet, Carbophenothion, Benoxafos, Azinphos-methyl, Azinphos-ethyl, Amiton, Amidithion, Cyanthoate, Dialiphos, Dimethoate, Dioxathion, Disulfoton, Endothion, Etion, Ethoate-methyl, Formothion, Malathion, Mercarbam, Omethoate, Oxydeprofos, Oxydisulfoton, Phenkapton, Phorate, Phosalone, Prothidathion, Prothoate, Sophamide, Thiometon, Vamidothion, Methamidophos.

The present invention is further described by the following examples that should not be construed as limiting the scope of the invention.

EXAMPLES

Chemicals used as buffers and substrates were commercial products of at least reagent grade.

Example 1

Cloning and Expression of DFPase Gene

Synthetic genes encoding the DFPases from *Aplysica californica* were designed and the gene were synthesized by a commercial supplier, and subsequently cloned into the expression vector pET30a+ by PCR as described below.

Cloning of the DFPases

The PCR primer set listed below was used to PCR amplify the synthetic DFPase gene. For cloning purposes the restriction sites NdeI and XhoI were introduced in the end of the PCR fragment (sites are underlined in the primer sequences listed below).

```
Primer 1:
                                    (SEQ ID NO: 3)
5'-ATATACATATGGCACCTACGGTTGTATCTCTTC-3'

Primer 2:
                                    (SEQ ID NO: 4)
5'-GTGCTCGAGGTTTTTGTCACAATACTGAGGC-3'
```

The PCR fragment was spin purified, digested with NdeI and XhoI (New England Biolabs) and ligated using T4 DNA ligase (New England Biolabs) into plasmid expression vector pET30a+ (InVitrogen) that first had been digested with NdeI and XhoI.

Following ON incubation at 16° C. the ligation reaction was transformed into competent *E. coli* TOP10 cells (Invitrogen) which were plated onto LB agar plates containing 20 µg/ml Kanamycin. Plates were incubated for 16 hours at 37° C.

Plasmid DNA were purified from selected transformants, and sequenced for verification of cloning procedure. Finally plasmid were transformed into competent *E. coli* BL21(DE3) cells for protein expression.

DFPase Expression

BL21(DE3) cells harboring the plasmid described above were inoculated into 20 ml TB-Glycerol medium supplemented with 20 µg/ml kanamycin (TBGK-medium) in 125 ml Erlenmeyer flasks. Cultures were grown overnight at 37° C. and 180 rpm.

Next day 2 liter Erlenmeyer flasks containing 1 liter TBGK-medium were inoculated with these cultures to an initial $OD_{600}$=0.1. Cultures were grown at 30° C. and 180 rpm until $OD_{600}$ reached 0.7, at which time IPTG was added to at a final concentration of 1 mM. Growth was continued for 16 hours at 30° C. and 180 rpm.

Example 2

Purification

Cells were harvested from the cultures by centrifugation at 5000 rpm for 10 minutes, and intracellular proteins were extracted using CelLytic protein extraction reagent (Sigma).

The lysed fermentation was filtered through a 0.22 µm bottle top filter (Nalgene). Solid NaCl, Tris-HCl and Imidazole were added to the following concentrations: 50 mM Tris-HCl, 20 mM Imidazole and 0.5 M NaCl. pH was adjusted to 7.4, and the solution purified using a chelating sepharose FF column preloaded with $Cu^{2+}$ on a Äkta purifier 900 system. Elution was performed step-wise with increasing Imidazole concentrations (0, 10%, 20% and 50% 500 mM imidazole).

Fractions belonging to the same peak were pooled, concentrated and buffer-changed into 50 mM TRIS, pH 7.0 using Amicon Ultra centrifugal filter devices with a 30 kDa cut-off.

Example 3

Measurement of Enzyme Activity

The DFPase activity was determined as follows:
The enzymatic activity was determined either by a pH stat assay as described in Blum et al, JACS 128 (2006): 12750-12757, or using in situ Fourier transform infrared spectroscopy as described in Gäb et al, Anal Biochem 385 (2009): 187-193. In the pH stat assay DFP hydrolysis was determined by a measuring the release of fluoride ions at 298 K in a nitrogen atmosphere. The assay was performed in 3 ml at pH 7.5, containing 10 mM NaCl and 10% acetonitrile. The reaction was initiated by addition of 2 microliter of 0.5 mg/mL DFPase. Initial velocities were determined at eight different substrate concentrations (0.5-10 mM), and corrected for the uncatalyzed rate of DFP hydrolysis. In situ Fourier transform infrared (FTIR) spectroscopy was used to measure real-time reaction rates of the nerve agent substrates when these were hydrolyzed to the corresponding phosphoric and phosphonic acids.

Hydrolysis of dihydrocoumarine was followed at 25° C. at 235 nm in a spectrophotometer by addition of purified DFPase to a solution containing 1 mM dihydrocoumarine in 50 mM Tris, 2 mM $CaCl_2$, pH 7.5. The specific activities of hydrolysis of dihydrocoumarine for the DFPases when calculated as decrease in absorbance at 235 nm per minute per mg of protein was calculated to be: 44 U/mg for *Aplysia californica* and 1.7 U/mg for *Loligo vulgaris*.

Qualitative Activity Test

The DFPase was tested with the following G-agents: DFP, Soman, Cyclosarin and Sarin. The *Aplysia* DFPase showed activity against all four G-agents.

| Substrate | Specific activity of *Loligo vulgaris* to substrate U/mg | Specific activity of *Aplysia californica* to substrate U/mg |
| --- | --- | --- |
| DFP (1.79%) | 305 | 43 |
| Sarin (1.97%) | 115 | 195 |
| Soman (1.89%) | 95 | 198 |
| Cyclosarin (1.9%) | 205 | 263 |
| Coumarine | 1.7 | 44 |

As can be seen from the table the DFPase from *Aplysia californica* has better activity on Sarin, Soman and Cyclosarine despite it has lower activity on DFP.

DEPOSIT OF BIOLOGICAL MATERIAL

The following biological material has been deposited under the terms of the Budapest Treaty with the Deutsche Sammlung von Mikroorganismen and Zellkulturen GmbH (DSM), and given the following accession number:

| Deposit | Accession Number | Date of Deposit |
| --- | --- | --- |
| *E. coli* NN059104 | DSM 22525 | Apr. 28, 2009 |

The strain has been deposited under conditions that assure that access to the culture will be available during the pendency of this patent application to one determined by foreign patent laws to be entitled thereto. The deposit represents a substantially pure culture of the deposited strain. The deposit is available as required by foreign patent laws in countries wherein counterparts of the subject application or its progeny are filed. However, it should be understood that the availability of a deposit does not constitute a license to practice the subject invention in derogation of patent rights granted by governmental action.

The invention described and claimed herein is not to be limited in scope by the specific aspects herein disclosed, since these aspects are intended as illustrations of several aspects of the invention. Any equivalent aspects are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

The invention claimed is:

1. An isolated polypeptide having organophosphorous hydrolase activity, selected from the group consisting of:
   (a) a polypeptide comprising an amino acid sequence having at least 90% sequence identity to the mature polypeptide of SEQ ID NO: 2;
   (b) a polypeptide encoded by a polynucleotide that hybridizes under at least medium-high stringency conditions with (i) the mature polypeptide coding sequence of SEQ ID NO: 1, (ii) a DNA sequence comprising the mature polypeptide coding sequence of SEQ ID NO: 1, or (iii) a full-length complementary strand of (i) or (ii), wherein medium-high stringency conditions are defined as prehybridization and hybridization at 42° C. in 5×SSPE, 0.3% SDS, 200 μg/ml sheared and denatured salmon sperm DNA, and 35% formamide and a wash three times, each for 15 minutes using 2×SSC, 0.2% SDS at 60° C.; and
   (c) a polypeptide encoded by a polynucleotide comprising a nucleotide sequence having at least 90% sequence identity to the mature polypeptide coding sequence of SEQ ID NO: 1.

2. The polypeptide of claim 1, comprising or consisting of the amino acid sequence of SEQ ID NO: 2; or a fragment thereof having organophosphorous hydrolase activity.

3. The polypeptide of claim 2, comprising or consisting of the mature polypeptide of SEQ ID NO: 2.

4. The polypeptide of claim 1, which is encoded by a polynucleotide comprising or consisting of the nucleotide sequence of SEQ ID NO: 1; or a subsequence thereof encoding a fragment having organophosphorous hydrolase activity.

5. The polypeptide of claim 4, which is encoded by a polynucleotide comprising or consisting of the mature polypeptide coding sequence of SEQ ID NO: 1.

6. A nucleic acid construct comprising a nucleotide sequence encoding the polypeptide of claim 1, said encoding nucleic acid operably linked to one or more control sequences that direct the production of the polypeptide in an expression host.

7. A recombinant expression vector comprising the nucleic acid construct of claim 6.

8. A isolated recombinant host cell comprising the nucleic acid construct of claim 6, or comprising the expression vector of claim 7.

9. A method of producing the polypeptide of claim 1, comprising: (a) cultivating a cell, which in its wild-type form produces the polypeptide, under conditions conducive for production of the polypeptide; and (b) recovering the polypeptide.

10. A method of producing the polypeptide of claim 1, comprising: (a) cultivating a host cell comprising a nucleic acid construct comprising a nucleotide sequence encoding the polypeptide under conditions conducive for production of the polypeptide; and (b) recovering the polypeptide.

11. A method of producing a protein, comprising: (a) cultivating the recombinant host cell of claim 8 under conditions conducive for production of the protein; and (b) recovering the protein.

12. A composition comprising a polypeptide according to claim 1.

13. The composition according to claim 12, wherein the composition is a microemulsion or a lotion.

14. A method of using a polypeptide of claim 1 or a composition of claim 12 or 13 comprising decontaminating an area or a device contaminated with at least one harmful or undesired organophosphorous compound, wherein the at least one harmful or undesired organophosphorous compound is selected among G-agents, V-agents and pesticides.

15. A method for removing organophosphorous compound comprising contacting a polypeptide according to claim 1 or the composition according to claim 12 with the organophosphorous compound.

16. The isolated polypeptide of claim 1, wherein a polypeptide comprises an amino acid sequence having at least 95% sequence identity to the mature polypeptide of SEQ ID NO: 2.

17. The isolated polypeptide of claim 1, wherein a polypeptide comprises an amino acid sequence having at least 99% sequence identity to the mature polypeptide of SEQ ID NO: 2.

* * * * *

SEQUENCE LISTING

```
<160> NUMBER OF SEQ ID NOS: 4

<210> SEQ ID NO 1
<211> LENGTH: 930
<212> TYPE: DNA
<213> ORGANISM: Aplysia californica
<220> FEATURE:
<221> NAME/KEY: CDS
<222> LOCATION: (1)..(927)
<220> FEATURE:
<221> NAME/KEY: mat_peptide
<222> LOCATION: (1)..(927)

<400> SEQUENCE: 1 atg gct ccc aca gtc gtc tct cta cag ttt tca aaa att att gac gat      48
Met Ala Pro Thr Val Val Ser Leu Gln Phe Ser Lys Ile Ile Asp Asp
1               5                   10                  15 gta tca gga gca gaa ggc cca gtg ttt gac agt aac ggc act ttt tat      96
Val Ser Gly Ala Glu Gly Pro Val Phe Asp Ser Asn Gly Thr Phe Tyr
                20                  25                  30 gtt gtt gct cct gga gta aga aaa gat gca aag ccg gct ggt cag gtc     144
Val Val Ala Pro Gly Val Arg Lys Asp Ala Lys Pro Ala Gly Gln Val
            35                  40                  45 gtc cga att gac ctg agc tca gga cag aaa act gtt ttg tgt gag cct     192
Val Arg Ile Asp Leu Ser Ser Gly Gln Lys Thr Val Leu Cys Glu Pro
        50                  55                  60 cag gtt aac ggt gat ggg gga att ccg tgt ggt tgc caa gct gac aag     240
Gln Val Asn Gly Asp Gly Gly Ile Pro Cys Gly Cys Gln Ala Asp Lys
65                  70                  75                  80
```

```
cag ggc aac tta tat gtc gct gac atg agg ctg gga atc ttg aaa gtc      288
Gln Gly Asn Leu Tyr Val Ala Asp Met Arg Leu Gly Ile Leu Lys Val
                85                  90                  95 aaa cct aat gga gaa ttc acg cag gtg gca aga gta gac gag gga gga      336
Lys Pro Asn Gly Glu Phe Thr Gln Val Ala Arg Val Asp Glu Gly Gly
            100                 105                 110 agg acc atg cag ggc tgt aat gac tgt agc ctc gac tat acc ggg aac      384
Arg Thr Met Gln Gly Cys Asn Asp Cys Ser Leu Asp Tyr Thr Gly Asn
        115                 120                 125 ctg tgg gtc acg gca cca gct ggt gac ata gcc ccg agt gaa ttc aag      432
Leu Trp Val Thr Ala Pro Ala Gly Asp Ile Ala Pro Ser Glu Phe Lys
    130                 135                 140 atg tcg ttt cag gaa agt att ggt tcg att tac tgc ttg act tca gag      480
Met Ser Phe Gln Glu Ser Ile Gly Ser Ile Tyr Cys Leu Thr Ser Glu
145                 150                 155                 160 gga aaa gtg gtt cat ttg gac aca ggg ctc aga ttc cca aac ggt ata      528
Gly Lys Val Val His Leu Asp Thr Gly Leu Arg Phe Pro Asn Gly Ile
                165                 170                 175 gct gtc att cat gac gca aac agg cgg ccg gta aag ctc ata gtg gca      576
Ala Val Ile His Asp Ala Asn Arg Arg Pro Val Lys Leu Ile Val Ala
            180                 185                 190 gaa acg ccg acg cga ctc ctc ttg gcc tat gac att caa gga cct gga      624
Glu Thr Pro Thr Arg Leu Leu Leu Ala Tyr Asp Ile Gln Gly Pro Gly
        195                 200                 205 tta gtc gct aat aaa acg aaa tgg gcc aaa ttg cca gat tgt gag caa      672
Leu Val Ala Asn Lys Thr Lys Trp Ala Lys Leu Pro Asp Cys Glu Gln
    210                 215                 220 gaa ggt ggc cca gat gga atg gac ttt gac gat gcg gga aat ttg ctg      720
Glu Gly Gly Pro Asp Gly Met Asp Phe Asp Asp Ala Gly Asn Leu Leu
225                 230                 235                 240 gtg gct cac tgg ggt gcc ggg cac atc gaa gtg ttt ggt ccg gac gga      768
Val Ala His Trp Gly Ala Gly His Ile Glu Val Phe Gly Pro Asp Gly
                245                 250                 255 ggc gaa ccg atc aag cgt atc aag tgt cct ttt gac aag ccg agc aat      816
Gly Glu Pro Ile Lys Arg Ile Lys Cys Pro Phe Asp Lys Pro Ser Asn
            260                 265                 270 gtg cat ttt gag cca aac tcc aac atc gtg tac gtg acg gag cac acg      864
Val His Phe Glu Pro Asn Ser Asn Ile Val Tyr Val Thr Glu His Thr
        275                 280                 285 aac aac gcc cta tgg aag ttc cag tgg gag aac aag ggc atg cct cag      912
Asn Asn Ala Leu Trp Lys Phe Gln Trp Glu Asn Lys Gly Met Pro Gln
    290                 295                 300 tat tgt gac aaa aac tga                                              930
Tyr Cys Asp Lys Asn
305

<210> SEQ ID NO 2
<211> LENGTH: 309
<212> TYPE: PRT
<213> ORGANISM: Aplysia californica

<400> SEQUENCE: 2

Met Ala Pro Thr Val Val Ser Leu Gln Phe Ser Lys Ile Ile Asp Asp
1               5                   10                  15

Val Ser Gly Ala Glu Gly Pro Val Phe Asp Ser Asn Gly Thr Phe Tyr
            20                  25                  30

Val Val Ala Pro Gly Val Arg Lys Asp Ala Lys Pro Ala Gly Gln Val
        35                  40                  45

Val Arg Ile Asp Leu Ser Ser Gly Gln Lys Thr Val Leu Cys Glu Pro
    50                  55                  60
```

Gln Val Asn Gly Asp Gly Ile Pro Cys Gly Cys Gln Ala Asp Lys
65                  70                  75                  80

Gln Gly Asn Leu Tyr Val Ala Asp Met Arg Leu Gly Ile Leu Lys Val
            85                  90                  95

Lys Pro Asn Gly Glu Phe Thr Gln Val Ala Arg Val Asp Glu Gly Gly
                100                 105                 110

Arg Thr Met Gln Gly Cys Asn Asp Cys Ser Leu Asp Tyr Thr Gly Asn
            115                 120                 125

Leu Trp Val Thr Ala Pro Ala Gly Asp Ile Ala Pro Ser Glu Phe Lys
            130                 135                 140

Met Ser Phe Gln Glu Ser Ile Gly Ser Ile Tyr Cys Leu Thr Ser Glu
145                 150                 155                 160

Gly Lys Val Val His Leu Asp Thr Gly Leu Arg Phe Pro Asn Gly Ile
                165                 170                 175

Ala Val Ile His Asp Ala Asn Arg Arg Pro Val Lys Leu Ile Val Ala
                180                 185                 190

Glu Thr Pro Thr Arg Leu Leu Leu Ala Tyr Asp Ile Gln Gly Pro Gly
                195                 200                 205

Leu Val Ala Asn Lys Thr Lys Trp Ala Lys Leu Pro Asp Cys Glu Gln
210                 215                 220

Glu Gly Gly Pro Asp Gly Met Asp Phe Asp Asp Ala Gly Asn Leu Leu
225                 230                 235                 240

Val Ala His Trp Gly Ala Gly His Ile Glu Val Phe Gly Pro Asp Gly
                245                 250                 255

Gly Glu Pro Ile Lys Arg Ile Lys Cys Pro Phe Asp Lys Pro Ser Asn
                260                 265                 270

Val His Phe Glu Pro Asn Ser Asn Ile Val Tyr Val Thr Glu His Thr
                275                 280                 285

Asn Asn Ala Leu Trp Lys Phe Gln Trp Glu Asn Lys Gly Met Pro Gln
290                 295                 300

Tyr Cys Asp Lys Asn
305

<210> SEQ ID NO 3
<211> LENGTH: 33
<212> TYPE: DNA
<213> ORGANISM: Artificial sequence
<220> FEATURE:
<223> OTHER INFORMATION: primer 1

<400> SEQUENCE: 3
atatacatat ggcacctacg gttgtatctc ttc                              33

<210> SEQ ID NO 4
<211> LENGTH: 31
<212> TYPE: DNA
<213> ORGANISM: Artificial sequence
<220> FEATURE:
<223> OTHER INFORMATION: primer 2

<400> SEQUENCE: 4
gtgctcgagg tttttgtcac aatactgagg c                                31